United States Patent [19]

Martin et al.

[11] Patent Number: 5,514,361
[45] Date of Patent: May 7, 1996

[54] METHOD FOR MAKING A SYNTHETIC MEIXNERITE PRODUCT

[75] Inventors: Edward S. Martin, New Kensington; Alan Pearson, Murrysville, both of Pa.

[73] Assignee: Aluminum Company of America, Pittsburgh, Pa.

[21] Appl. No.: 235,504

[22] Filed: Apr. 29, 1994

[51] Int. Cl.⁶ ...................................................... C01F 7/16
[52] U.S. Cl. .................................................... 423/600
[58] Field of Search ........................... 423/600; 501/119, 501/120

[56] References Cited

U.S. PATENT DOCUMENTS

| Re. 34,164 | 1/1993 | Misra | 423/600 |
|---|---|---|---|
| 3,539,306 | 11/1970 | Kumura et al. | 23/315 |
| 4,239,656 | 12/1980 | Fujitani et al. | 423/213.5 |
| 4,637,995 | 1/1987 | DeAngelis et al. | 502/439 |
| 4,970,191 | 11/1990 | Schutz | 502/341 |
| 5,077,032 | 12/1991 | Mizukami et al. | 423/625 |
| 5,227,020 | 7/1993 | Endres et al. | 162/8 |
| 5,240,890 | 8/1993 | Ino et al. | 502/64 |

FOREIGN PATENT DOCUMENTS

| 583742 | 9/1959 | Canada | 423/600 |
|---|---|---|---|
| 92-00246 | 1/1992 | WIPO | 423/600 |

OTHER PUBLICATIONS

"The System $M_gO$–$AL_2O_3$–$H_2O$ and Influence of Carbonate and Nitrate Ions on the Phase Equilibria" May 1958.
"New Route to layered double hydroxides intercalated by organic anions: precursors to polyoxometalate–pillared derivatives" Jun. 1990 Inorganic Chemistry 29(13) 1990.
"Synthesis of Disordered and Al–Rich Hydrotalcite–Like Compounds" 1986 (no month).
"A new synthesis and characterization of magnesium–aluminum hydroxides" Mar. 1980.
"Hydrotalcite–Type Anionic Clays: Preparation, Properties and Applications" 1991 (no month).
"Meixnerit, $Mg_6Al_2(OH)_{18}$ $4H_2O$, ein neues Magnesium–Aluminum–Hyroxid–Mineral" 1975 (no month).

*Primary Examiner*—Michael Lewis
*Assistant Examiner*—Stuart L. Hendrickson
*Attorney, Agent, or Firm*—Gary P. Topolosky

[57] ABSTRACT

There is disclosed an improved method for making synthetic meixnerite having reduced carbonate contamination levels and a x-ray diffraction pattern resembling that shown in FIG. 1, the meixnerite is made by combining magnesium oxide and transition alumina, preferably an activated alumina powder having a BET surface area of about 100 $m^2/g$ or greater, in a substantially carbonate-free environment.

3 Claims, 1 Drawing Sheet

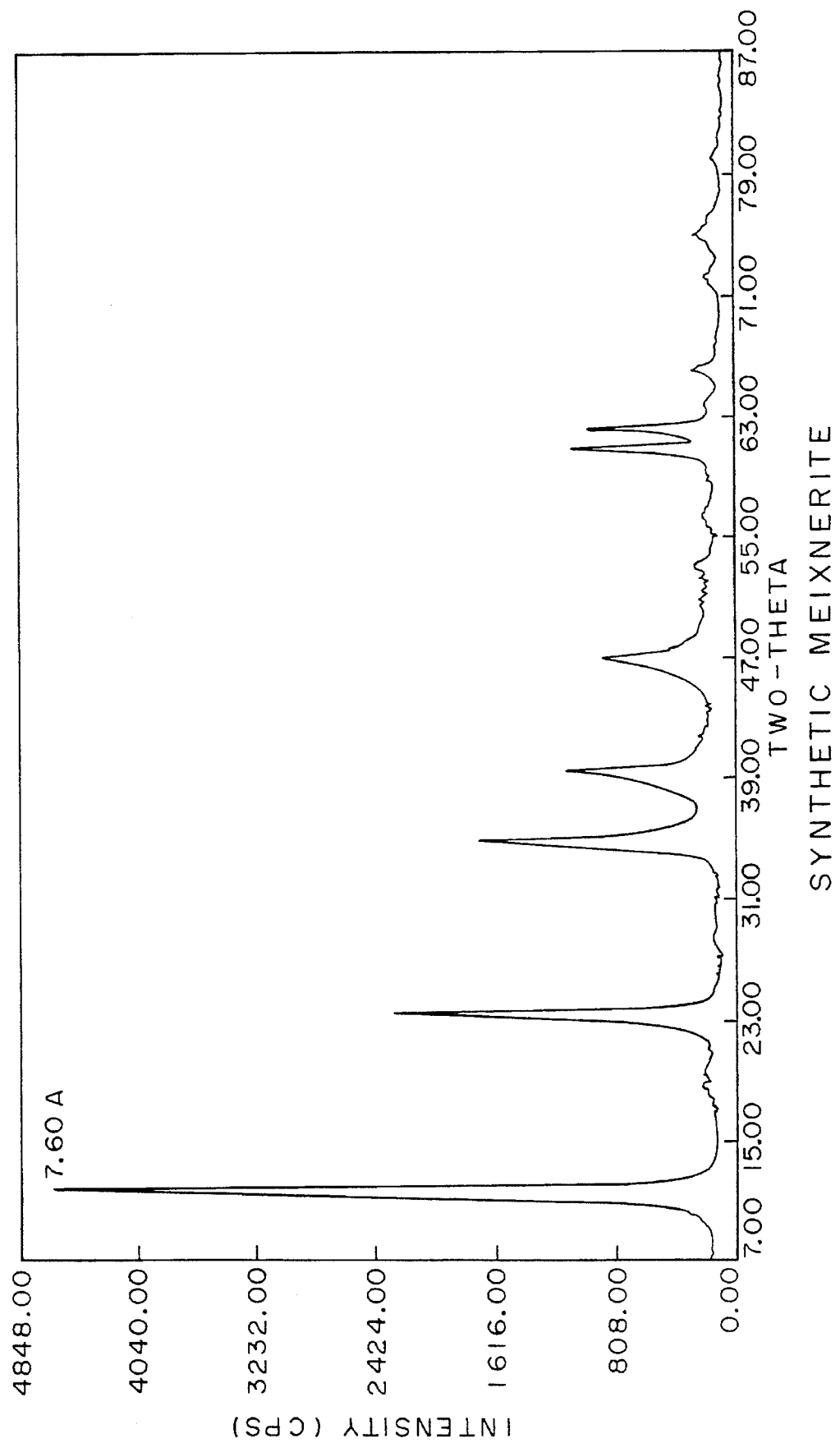

1

METHOD FOR MAKING A SYNTHETIC MEIXNERITE PRODUCT

BACKGROUND OF THE INVENTION

1. Field of the Invention

This invention relates to the field of making mixed metal hydroxides or layered double hydroxide compounds. More specifically, the invention relates to an improved synthetic meixnerite product and method for making the same.

2. Technology Review

Naturally occurring meixnerite exists as a secondly mineral in the cracks of serpentine rocks near Ybbs—Persenberg in lower Austria. In its crystalline state, such meixnerite material is tabular, colorless and has perfect basal cleavage. Natural meixnerite is closely related to hydrotalcite and pyroaurite in overall structure. Its infrared absorption spectrum compares favorably to those for hydrotalcite and other synthetic magnesium-aluminum double hydroxides. In some circles, meixnerite is even listed among other hydrotalcite-like materials, or grouped in the broader family of "hydrotalcites". Under the latter definition, meixnerite is a carbonate-free member of the hydrotalcite family which has only hydroxy anions. Still others refer to meixnerite as an all hydroxyl, layered double hydroxide.

Meixnerite, or magnesium aluminum hydroxide hydrate, is often symbolized by the formula $Mg_6Al_2(OH)_{18}.4H_2O$, although still other formulaic representations include: $Mg_4Al_2(OH)_{14}.3H_2O$ and $[Mg_3Al(OH)_8]OH.2H_2O$.

While the synthesis of meixnerite is fairly new, these various methods of manufacture do not appear to be commonly practiced or commercially practical. In March 1980, G. Mascolo et al. described a synthesis process in *Mineralogical Magazine* whereby magnesium oxide, decomposed from basic magnesium carbonate at 650° C. for 6 hours, was combined with an alumina gel and rotated in an air thermostated oven for one week at 80° C. The resulting product was then dried over silica gel. It was analyzed to contain some brucite compound and about 0.8–1.0 wt. % carbon dioxide.

Six years later, I. Pausch et al. wrote of a variation on the aforementioned process in *Clay and Clay Minerals*. Therein, magnesium oxide, annealed at 1050° C., was combined with an alumina gel ($\delta$—$Al_2O$), $MgC_2O_4.2H_2O$ and distilled water. This combination was heated to between 100°–350° C. at a pressure of 100 MPa for various reaction times ranging from 7 to 42 days. IR spectroscopy analysis of the resulting product showed some carbonate contamination, but at an intensity of less than 5% as compared to natural hydrotalcite.

From a series of experiments reported by E. Dimotakis et al. in *Inorganic Chemistry*, vol. 29, No. 13 (1990), synthetic meixnerite was prepared by calcining a hydrotalcite of the formula $[Mg_3Al(OH)_8][CO_3]_{0.5}.2H_2O$ at 500° C. to form a metal oxide solution. This oxide was then hydrolyzed at 25° C. in a carbon dioxide-free environment.

It is a principal objective of this invention to provide an improved means for making synthetic meixnerite. It is another objective to provide a process for synthesizing meixnerite and related minerals from two or more powders. It is still another objective to cream a hydrotalcite-like compound having significantly lower carbonate levels and virtually no other anion contamination. It is still another objective to provide a method for making synthetic meixnerite which is not dependent on the use of alumina gels. It is still another objective to make an improved meixnerite product from a transition alumina and an activated magnesia which has not been dead-burned or overly calcined.

On a preferred basis, synthetic meixnerite can be made from fairy inexpensive and readily available reactants by this process thus making it suitable for the commercial scale production of meixnerite and meixnerite-like materials. It is yet another objective to provide an improved meixnerite manufacturing process which outperforms (in terms of yield) other known methods including those involving magnesium carbonates, magnesium hydroxides and/or aluminum hydroxides.

SUMMARY OF THE INVENTION

In accordance with the foregoing objectives and advantages, there is provided an improved method for making synthetic meixnerite. The method comprises reacting a powdered magnesium oxide with a high surface area, transition alumina in a substantially carbonate-free solution or slurry. Such reaction causes a meixnerite-like compound to form. The latter compound may be removed from solution by filtering, centrifugation, vacuum dehydration or other known separation means. On a preferred basis, the transition alumina so combined with an activated magnesia consists essentially of an activated alumina powder having a surface area of about 100 $m^2/g$ or greater. For some double hydroxides, the powdered reactants that are being combined hereby may first be agglomerated before contact with water or steam. An improved synthetic meixnerite product made by the foregoing method is also disclosed.

BRIEF DESCRIPTION OF THE DRAWING

Further features, objectives and advantages will be made clearer from the following detailed description of preferred embodiments made with reference to the Figure which depicts an x-ray diffraction pattern for a meixnerite compound made by one embodiment of this invention.

DETAILED DESCRIPTION OF PREFERRED EMBODIMENTS

As used herein, the term "transition alumina" means a high surface area alumina in a powdered or fine particulate form. One preferred way of defining such alumina materials uses Surface Area and Loss on Ignition (LOI) measurement criteria. More specifically, an alumina having a Brunauer-Emmett-Teller [or B.E.T.] measured surface area of about 100 $m^2/g$ or more would be considered as having a high surface area and thus qualify as a transition alumina for purposes of this invention. Aluminas having an LOI weight percentage of about 1.5% or more would also qualify as a transition alumina under this definition while a typical $\delta$—$Al_2O_3$ would not.

One particular preferred type of transition aluminas is referred to as "rehydratable aluminas". They tend to form strong hydroxyl bonds on contact with water and their rehydration reactions are highly exothermic. The particle sizes for such aluminas may range from 0.01–200 μ, with a range of about 0.1 to 10 or 20 micrometers being more preferred.

Certain activated aluminas are more suitable than others for purposes of this invention. Most are high surface area aluminas formed by the rapid calcination of hydrated aluminas at temperatures below that required for complete dehydration or calcination. Typically, such aluminas are amorphous (i.e., have no microcrystalline structure) as determined by X-ray diffraction.

On a more preferred basis, the trivalent metal oxide powder combined with magnesia according to this invention is formed by the rapid dehydration of alumina trihydrate, typically by passing such trihydrate through a flame or hot gas for about 0.5 to several seconds. The resulting alumina derivative has an LOI value of about 4–12% by weight, and a BET surface area of about 200–300 m$^2$/g. One representative and preferred material is the line of activated alumina powders sold commercially by the Aluminum Company of America (Alcoa) under its CP Series designation. Such powder particulates are available in a variety of sizes. For such powders, the numeral following Alcoa's CP designation represents the average particle size for that product; thus, greater than 50% of the particles in Alcoa's CP-1 powder measure 1 micron or larger. For Alcoa's CP-2 powder, greater than 50% measure 2μ or more, and so on for Alcoa's CP-5, CP-7 and CP-100 product line.

As used herein, magnesia or magnesium oxide refers to the magnesium-based product activated by "soft burning" at one or more temperatures between about 450°–900° C. It generally has a surface area of 10–200 m$^2$/g, preferably about 25–150 m$^2$/g and an L.O.I. ranging from 1.0 to 6.0 wt. %. The percent carbon dioxide for such material generally ranges between 0.51 and 1.61%. Such criteria distinguishes this preferred product from activated magnesia which has been dead-burned or completely calcined. Although the latter may still produce meixnerite at longer reaction times and under more strenuous reaction conditions, the percent yields from such conditions are significantly lower than those resulting for the present invention. There are numerous means for making an activated magnesia product to combine with transition aluminas according to this invention. For example, commercially sold magnesium carbonate can be heated to drive off carbon dioxide and thus form a reactive magnesia thereby. Magnesium oxide may also be made by heating either natural or synthetic magnesium hydroxides to temperatures between 380°–950° C., or basic magnesium carbonate by heating $MgCl_2$ with lime. Various methods known to those skilled in the art may be used to generate magnesia powders of various particles sizes and/or surface areas.

As used herein, the term "carbonate contamination" pertains to the level of carbonate (or $CO_3^{-2}$) in the final product. Sometimes, this is stated as a percent carbon which must be converted to a more representative level of actual carbonate contamination. Still other divalent metal oxides, such as CaO, may be combined with transition aluminas or other powdered trivalent metal oxides according to the aforementioned methods.

One way of summarizing this mechanism is by the following chemical reaction: $6MgO+Al_2O_3.XH_2O+12H_2O \rightarrow Mg_6Al_2(OH)_{16}(OH)_2.(3+x)H_2O$ wherein x ranges from about 0.1 to about 1.0. It is preferrred that pH's be maintained at a level of 11 or higher in order to enhance overall solubility of the transition alumina reactant. Still other temperature limitations on the contacting water solution have also proven beneficial to overall yield. It is preferred that this reaction proceed at one or more temperatures between about 80° and 180° C. At such temperatures, yields in excess of about 85 to 90% are commonly observed. More preferred reaction temperatures generally run between about 95°–150° C.

There are various end uses for the products made by the method of this invention. Most notably, such compounds can be converted into hydrotalcite or a hydrotalcite-like material through contact with carbonate or another anion substitute.

EXAMPLES

Each of the following examples were conducted at two temperatures: atmospheric boiling (or 98° C.) and 150° C. Considerable conversion occurs after 2 hours at atmospheric boiling. But even greater conversion was observed after 22.8 hours (based on X-ray diffraction patterns). A better crystallized magnesium aluminum layered double hydroxide was made by heating a slurry mixture of magnesium oxide and alumina to 150° C. for 2 hours or more.

EXAMPLE 1

Using Activated Alumina and Magnesium Oxide

Magnesium oxide was prepared by heating hydromagnesite sold by Fisher Scientific and having the formula $Mg_5(CO_3)_4(OH)_2.4H_2O$, for 2 hours at about 475° C.

a. Reaction at atmospheric boiling:

About 52.5 grams of this MgO was charged into a reactor with 34.2 grams of Alcoa CP-2 activated alumina (having an average particle size of 2 microns. The contents of this reactor were then stirred constantly and heated for 4 hours at 60° C. The reactor temperature was then raised to 98° C. and held there for an additional 18.5 hours. A sample of the slurry taken 2 hours after the reaction mixture reached 98° C. was then filtered, and the solids dried at 105° C. X-ray diffraction analysis showed that the solids so produced were mostly meixnerite-like, with some magnesium hydroxide present. The slurry reaction mixture was stirred and heated for another 16 hours before cooling and filtering. The filter cake was then dried overnight at 105° C. X-ray diffraction analysis showed that the latter filter cake solid was mostly meixnerite, with some residual magnesium hydroxide.

b. Reaction at 150° C.:

Another slurry of the same composition as above was stirred constantly and heated to 60° C., then held at that temperature for 4 hours. The temperature was then increased to 150° C. and kept there for another 18.8 hours. A slurry sample taken 2 hours after the reaction mixture reached 150° C. contained meixnerite and some converted $Mg(OH)_2$. Two more samples taken from the solids as the cooled reaction slurry was filtered, showed only a meixnerite-like material forming.

EXAMPLE 2

Using Pelletized MgO and Activated Alumina

About 52.5 g of magnesium oxide and 34.2 of activated alumina were mixed in a Turbula powder mixer for 2 hours. The blended powders were then formed into an agglomerate, or more specifically pellets, using a hydraulic press and about 5,000 pounds of pressure. The resulting pellets had a diameter of about 0.40 inch (10.2 mm) and required about 0.50 grams of mixed powder to form.

a. Reaction at atmospheric boiling.

Ten pellets, formed as described above, were placed in a beaker under a layer of deionized water. The system was brought to atmospheric boiling (by heating to one or more temperatures between about 80°–180° C. (176°–356° F.)) and kept there for about 2 hours. The only stirring was from turbulence due to the boiling water. One pellet separated into three pieces, another into two. The rest remained whole though several had cracks perpendicular to the direction of pressing. According to X-ray diffraction analysis, the pellets included meixnerite-like compounds, a minor amount of $Mg(OH)_2$, and trace amounts of MgO.

b. Reaction in liquid water at 150° C.

Ten more of the foregoing pellets were placed in a Parr pressure reactor with some deionized water. The reactor was then closed, heated to about 150° C. and held at that temperature for about 2 hours. After the reactor cooled, the pellets were removed and dried overnight at 110° C. in a vacuum oven. Upon X-ray diffraction analysis, the pellets contained a meixnerite-like compound and minor amounts of boehmite.

EXAMPLE 3

Using Magnesite and Activated Alumina

A mineral sample containing magnesite, dolomite, and quartz was ground to minus 325 mesh (44 micrometers) and calcined for 2 hours at 700° C., thus resulting in a total weight loss of 46.5%. Analysis of this material showed about 16.9 wt. % magnesium, about 5.66 wt. % calcium, about 1.75 wt. % silicon, and about 0.4 wt. % iron (Mg, Ca, and Si were measured by atomic absorption; and the iron by qualitative spectroscopy). The carbon dioxide content was found to be 46.2% by LECO analysis.

The reactor charge consisted of 750 ml of deionized water, 34.2 grams of Alcoa CP-2 alumina, and 61.8 grams of the latter calcined magnesite. The resulting slurry was placed in a Parr autoclave reactor and stirred constantly while being heated for 4 hours at 60° C.

a. At atmospheric boiling

After heating to atmospheric boiling for 2 hours, a slurry sample was withdrawn. The end contents were then filtered, dried at 110° C. overnight and sampled for analysis. According to x-ray diffraction, the solids consisted of meixnerite-like materials and tricalcium aluminate with trace quantities of quartz.

b. At 150° C.:

The reaction slurry was heated to 150° C. and a slurry sample withdrawn after 2 hours. The reactor contents were then filtered at the end of the run and a sample of filter cake taken for analysis. Both samples were dried at 110° C. overnight. Each solid consisted of a major amount of meixnerite-like material, tricalcium aluminate, a trace amount of quartz, and traces of boehmite according to x-ray diffraction analysis.

For comparative purposes, several meixnerite samples were prepared using an Al(OH), starting material in combination with the magnesium oxide described in above EXAMPLE 1. These samples did not perform as well as the transition alumina-prepared samples using a direct comparative chromate ($CrO_4^{2-}$) absorption test (for approximating the relative amounts of meixnerite-like materials present in the resulting products).

TABLE

| Sample | Aluminum Source | Formation Time (hrs) | Chrome Load (%) [vs. Std.] |
|---|---|---|---|
| A | CP-2 alumina | 18.5 | 11.64 [6.82] |
| B | Al(OH)$_3$ | 21.75 | 7.90 [8.52] |
| C | Al(OH)$_3$ | 22.17 | 7.45 [8.52] |

Having described the presently preferred embodiments, it is to be understood that the invention may be otherwise embodied within the scope of the appended claims.

What is claimed is:

1. A method for making synthetic meixnerite comprises:
   (a) reacting powdered magnesium oxide with a transition alumina having a B.E.T. surface area of about 100 m$^2$/g or more in a substantially carbonate-free solution to form a meixnerite compound, said reacting including the steps of:
     (i) combining the magnesium oxide and transition alumina into an agglomerate; and
     (ii) exposing said agglomerate to liquid water heated to one or more temperatures between about 80°–180° C. (176°–356° F.); and
   (b) separating said meixnerite compound from the solution.

2. The method of claim 1 wherein the transition alumina consists essentially of an activated alumina powder having a BET surface area of about 100 m$^2$/g or more.

3. The method of claim 1 wherein the magnesium oxide and transition alumina combined in step (i) are heated to one or more temperatures between about 50°–70° C. (122°–158° F).

* * * * *